(12) United States Patent
Ye

(10) Patent No.: US 12,728,226 B1
(45) Date of Patent: Sep. 8, 2026

(54) LIGHT EMITTING DIODE (LED) CONTROL DRIVE SYSTEM FOR SLEEP AID DEVICE

(71) Applicant: Xiaodong Ye, Wenzhou (CN)

(72) Inventor: Xiaodong Ye, Wenzhou (CN)

( * ) Notice: Subject to any disclaimer, the term of this patent is extended or adjusted under 35 U.S.C. 154(b) by 0 days.

(21) Appl. No.: 19/337,034

(22) Filed: Sep. 23, 2025

(51) Int. Cl.

| | |
|---|---|
| ***H02M 3/156*** | (2006.01) |
| ***A61M 21/02*** | (2006.01) |
| ***A61N 5/06*** | (2006.01) |
| ***H02J 7/62*** | (2026.01) |
| ***H05B 45/10*** | (2020.01) |
| ***H05B 45/325*** | (2020.01) |
| ***H05B 45/34*** | (2020.01) |
| ***H05B 45/345*** | (2020.01) |

(Continued)

(52) U.S. Cl.
CPC ........... *A61M 21/02* (2013.01); *A61N 5/0622* (2013.01); *H02J 7/62* (2026.01); *H02M 3/156* (2013.01); *H05B 45/10* (2020.01); *H05B 45/325* (2020.01); *H05B 45/34* (2020.01); *H05B 45/345* (2020.01); *H05B 45/36* (2020.01); *H05B 45/375* (2020.01); *H05B 47/195* (2020.01); *A61M 2021/0044* (2013.01); *A61M 2205/50* (2013.01); *A61N 2005/0627* (2013.01); *A61N 2005/0652* (2013.01); *A61N 2005/0663* (2013.01)

(58) Field of Classification Search
CPC .......... A61M 21/02; A61M 2021/0044; A61M 2205/50; A61N 5/0622; A61N 2005/0627; A61N 2005/0652; A61N 2005/0663; H02J 7/62; H05B 45/10; H05B 45/325; H05B 45/34; H05B 45/345; H05B 45/36; H05B 45/375; H05B 47/195; H02M 3/156
See application file for complete search history.

(56) References Cited

U.S. PATENT DOCUMENTS

2020/0030569 A1 * 1/2020 Grange ................. A61M 21/02

FOREIGN PATENT DOCUMENTS

CN 201726559 U * 1/2011
CN 102479489 A * 5/2012 ............ H05B 45/54

(Continued)

OTHER PUBLICATIONS

"LTC4090/LTC4090-5 USB Power Manager with 2A High Voltage Bat-Track Buck Regulator," Analog Devices, 2017 (Year: 2017).*

(Continued)

*Primary Examiner* — Jeffrey A Gblende
*Assistant Examiner* — Jye-June Lee
(74) *Attorney, Agent, or Firm* — JEEN IP LAW, LLC

(57) ABSTRACT

The present disclosure discloses a light emitting diode (LED) control drive system for a sleep aid device, including a universal serial bus (USB) interface module, a voltage regulator module, a power management module, an LED lamp assembly, a constant current drive module, an infrared module, and a touch module. The voltage regulator module converts an external input voltage into a stable direct current voltage through a conversion circuit, a filter circuit, and the like and charges a storage battery. The power management module detects in real time a charging state of the storage battery. A microcontroller of the constant current drive module receives infrared and touch commands and controls the brightness of the LED lamp assembly through a dimming circuit. The LEDs are red light LEDs with wavelengths of 625 nm±5 nm or yellow light LEDs with color temperatures of 1,800 K±100 K.

9 Claims, 4 Drawing Sheets

(51) Int. Cl.

| | |
|---|---|
| ***H05B 45/36*** | (2020.01) |
| ***H05B 45/375*** | (2020.01) |
| ***H05B 47/195*** | (2020.01) |
| *A61M 21/00* | (2006.01) |

(56) References Cited

FOREIGN PATENT DOCUMENTS

| | | | | | |
|---|---|---|---|---|---|
| CN | 104836271 | A | * | 8/2015 | .............. H02J 7/663 |
| CN | 105338694 | A | * | 2/2016 | |
| CN | 107943138 | A | * | 4/2018 | ............. G05D 23/20 |
| CN | 220421432 | U | * | 1/2024 | |

OTHER PUBLICATIONS ("P-MOSFET Buck Converter (Switching Power Supply)—CircuitLab", URL: https://www.circuitlab.com/circuit/23xkcx/p-mosfet-buck-converter-switching-power-supply/, 2012 (Year: 2012).*

* cited by examiner

LIGHT EMITTING DIODE (LED) CONTROL DRIVE SYSTEM FOR SLEEP AID DEVICE

TECHNICAL FIELD

The present disclosure relates to the technical field of LED drive control, and in particular to a light emitting diode (LED) control drive system for a sleep aid device.

BACKGROUND

With the accelerating rhythm of modern life, sleep disorder prevails increasingly. A phototherapy-based sleep aid device simulates natural illumination change by adjusting the brightness and color of an LED light source and has become an important tool to improve sleep. However, the LED drive system of an existing sleep aid device has many shortcomings. The conventional USB power supply mode is easily affected by voltage fluctuation, which results in unstable brightness of the LED, thereby affecting the sleep effect. Most drive systems use simple PWM to dim and cannot achieve constant current control, causing color temperature shift or shortened service life of the LED. Due to lack of intelligent control integrating infrared remote control and touch control, the user experience is poor. Moreover, the charging state of the storage battery is not monitored in real time, so that the reliability of the device may be affected by overcharging or over-discharging. Therefore, there is an urgent need for an LED drive system that features high stability, high-precision dimming, and intelligent control, with an aim to effectively enhance the practicality and user experience of the sleep aid device by optimizing power management, improving the dimming precision, and enriching the interactive mode.

SUMMARY

The present disclosure aims to provide a light emitting diode (LED) control drive system for a sleep aid device, which achieves stable light color output and convenient user interaction through power management optimization, constant current drive, and intelligent dimming technology, so as to improve the sleep aid effect.

In order to overcome shortcomings in the above technology, the present disclosure adopts the following technical solutions:

a light emitting diode control drive system for a sleep aid device, including:

a universal series bus (USB) interface module 1, configured to receive an external input voltage;

a voltage regulator module 2, connected to the USB interface module 1, including a conversion circuit 21, a filter circuit 22, and a storage battery 23, and configured to convert the external input voltage into a stable direct current voltage and charge the storage battery, so as to provide a stable power supply basis;

a power management module 3, including a power control chip U1, where the power control chip U1 is connected to the voltage regulator module 2 and configured to control a working state of the conversion circuit 21 and detect in real time a charging state of the storage battery 23, so as to guarantee the power supply stability by dynamic regulation;

an LED lamp assembly 4, provided with a plurality of sleep aid LEDs 41; and a constant current drive module 5, including a microcontroller U2 and a dimming circuit 51, the microcontroller U2 being connected to an infrared module 6 and a touch module 7 and configured to receive a user input command, where a control terminal of the dimming circuit 51 is connected to the microcontroller U2 and an output terminal of the dimming circuit is connected to the LED lamp assembly 4, and the dimming circuit is configured to control a brightness of the LED lamp assembly 4 according to a command of the microcontroller U2 based on the stable power supply basis, so as to avoid a voltage fluctuation impact.

Further, the LEDs 41 are red light LEDs with wavelengths of 625 nm±5 nm or yellow light LEDs with color temperatures of 1,800 K±100 K.

Further, the conversion circuit 21 includes an inductor L1, an N-channel metal oxide semiconductor (MOS) transistor Q2, a Schottky diode D1, a P-channel MOS transistor Q1, an NPN triode Q3, a first resistor R1, an eighth resistor R8, a ninth resistor R9, an eleventh resistor R11, and a twelfth resistor R12;

a source of the N-channel MOS transistor Q2 is electrically connected to a VIN output terminal of the USB interface module 1, a drain of the N-channel MOS transistor L1 is electrically connected to a first terminal of the inductor D1 and an anode of the Schottky diode, respectively, and a cathode of the Schottky diode is grounded; a gate of the N-channel MOS transistor is electrically connected to a first terminal of the first resistor D1, a second terminal of the first resistor R1 is electrically connected to a source S of the N-channel MOS transistor Q2 and the first resistor is configured to convert a high voltage outputted by the USB interface module 1 into a low regulated voltage by regulating a duty cycle of a pulse width modulation (PWM) signal to supply power to a subsequent circuit;

a second terminal of the inductor L1 is electrically connected to a drain of the P-channel MOS transistor Q1 and a first terminal of the twelfth resistor R12, respectively, and a second terminal of the twelfth resistor R12 is grounded; and a source of the P-channel MOS transistor Q1 is electrically connected to an output terminal B+ of the conversion circuit 21 and a first terminal of the eighth resistor R8, the gate G is respectively connected to a second terminal of the eighth resistor R8 and a collector of the NPN triode Q3 and configured to achieve a synchronous rectification function, so as to improve electric energy conversion efficiency of the conversion circuit; and a base of the NPN triode Q3 is electrically connected to a control terminal of the power management module 2 through the ninth resistor R9; an emitter of the NPN triode Q3 is electrically connected to ground and the eleventh resistor R11 is connected in series between the base of the NPN triode Q3 and the emitter and configured to eliminate a residual charge in a base region and suppress noise interference, so as to stabilize an on-off state of the Q3. The P-channel MOS transistor Q1 is conducted when being turned off on the N-channel MOS transistor Q2 to achieve synchronous rectification.

Further, the filter circuit 22 includes a first capacitor C1 and a sixth capacitor C6, where a first terminal of the first capacitor C1 is electrically connected to the VIN output terminal of the USB interface module 1, and a second terminal of the first capacitor C1 is electrically connected to ground and configured to filter high frequency ripple noise in an input voltage of the USB and smooth a waveform of the input voltage, so as to prevent power interference from affecting system stability; and a first terminal of the sixth capacitor C6 is electrically connected to an output terminal B+ of the conversion circuit 21, and a second terminal is electrically connected to ground and configured to store electric energy outputted by the conversion circuit 21, supply power to the storage battery BT1 continuously during discharge of the inductor L1, and smooth the boosted direct current voltage, so as to reduce a ripple factor of the output voltage.

Further, the voltage regulator module 2 further includes a voltage feedback circuit 24 and a current sampling circuit 25, where the voltage feedback circuit 24 includes a second resistor R2 and a fourth resistor R4;

a first terminal of the second resistor R2 is electrically connected to the output terminal B+ of the conversion circuit 21, and a second terminal of the second resistor R2 is electrically connected to a first terminal of the resistor R4 and a voltage feedback terminal of the power control chip 31 of the power management module 3, respectively; a second terminal of the resistor R4 is electrically connected to ground and configured to divide the input voltage and feed the input voltage back to the chip 31; and the current sampling circuit 25 includes a fifth resistor R5, and the fifth resistor R5 is connected in series between a negative terminal of the storage battery 23 and the ground and configured to monitor in real time a discharge current of the storage battery 23.

Further, the power control chip U1 is model ZW46103, and the power control chip includes:

a switch driver output pin SW, electrically connected to the gate of the N-channel MOS transistor Q2 and configured to output a high frequency PWM pulse signal to control the Q2;

an enable control pin CEN, electrically connected to a first terminal of the ninth resistor R9, where a second terminal of the ninth resistor R9 is electrically connected to the base of the NPN triode Q3 in the conversion circuit and configured to send an enable signal and control conduction of the NPN triode Q3, so as to achieve start-stop control of the conversion circuit 21; and a voltage feedback regulation pin VFB, electrically connected to a public node of the second resistor R2 and the fourth resistor R4 through the second capacitor C2, and configured to collect a voltage division signal of the output voltage of the conversion circuit 21 and dynamically adjust the PWM duty cycle according to a comparison result to achieve constant voltage control.

Further, the LEDs 41 are divided into a plurality of groups in parallel, each group of the LEDs is connected in series to current limiting resistors, and the current limiting resistors include a thirteenth resistor R13, a fourteenth resistor R14, an eighteenth resistor R18, and a twentieth resistor R20;

first terminals of the thirteenth resistor R13, the fourteenth resistor R14, the eighteenth resistor R18, and the twentieth resistor R20 are electrically connected to anodes of the LEDs in different groups, respectively, and second terminals thereof are commonly electrically connected to the output terminal B+ of the conversion circuit 21 and configured to achieve independent constant control of each group of the LEDs.

Further, the dimming circuit 51 includes an N-channel MOS transistor Q4, a fifteenth resistor R15, and a sixteenth resistor R16, where a first terminal of the fifteenth resistor R15 is electrically connected to a PWM dimming output terminal of the microcontroller U2 of the constant current drive module 5, and a second terminal of the fifteenth resistor R15 is electrically connected to a gate of the N-channel MOS transistor Q4; a first terminal of the sixteenth resistor R16 is electrically connected to the gate of the N-channel MOS transistor Q4, and a second terminal of the sixteenth resistor R16 is electrically connected to ground; and a drain of the N-channel MOS transistor Q4 is electrically connected to a cathode common terminal of the LED lamp assembly 4, and a source of the N-channel MOS transistor Q4 is grounded.

Further, the microcontroller U2 is model ZW8P98001, and the microcontroller includes:

an infrared signal receiving pin T1, electrically connected to a signal output terminal of the infrared module 6 and configured to receive a demodulated infrared remote control command;

a PWM dimming output pin T2, electrically connected to a control terminal LEDW of the dimming circuit 51 and configured to output a variable duty cycle PWM signal to adjust an overall brightness of the LED lamp assembly 4; and a touch input pin T3, electrically connected to an input terminal of the touch module through a twenty-first resistor R21 (1 KΩ and configured to receive a touch operation signal.

Further, the power management module 3 further includes a sixth resistor R6 and an eighth capacitor C8, where a first terminal of the sixth resistor R6 is electrically connected to the VIN output terminal of the USB interface module 1, and a second terminal thereof is electrically connected to a first terminal of the eighth capacitor C8; a second terminal of the eighth capacitor C8 is grounded; a common node of the sixth resistor R6 and the eighth capacitor C8 is electrically connected to a power input terminal VIN of the power control chip U1; and a ground terminal GND of the power control chip U1 is directly electrically connected to ground.

Compared with the prior art, the present disclosure has the following beneficial effects:

1. Through the collaborative design of the conversion circuit and the dual-stage filter circuit in the voltage regulator module, matched with the dynamic voltage feedback mechanism of the power management chip, an integral voltage regulation architecture is built to solve the problem that the brightness of the LEDs is unstable due to voltage fluctuation in the conventional USB power supply mode, thereby providing a stable power basis for sleep aid phototherapy.
2. By using the drive architecture in which grouped current limiting resistors and the dimming circuit are combined, the currents of the LEDs are precisely adjusted through the PWM signal outputted from the microcontroller, so that the limitation that the constant current cannot be achieved by simple PWM dimming in the prior art is overcome, the color temperature shift and the shortened service life of the LEDs caused by current drift are avoided, and the reliability of the drive circuit is improved.
3. The power management module achieves dynamic management of the charging state of the storage battery through the real-time monitoring mechanisms of the chip and the sampling circuit and forms the overcharge and over-discharge protection function, thereby optimizing the defects in extensive energy management in the prior art, prolonging the service life of the storage battery, and improving the reliability of the device.

4. The infrared and touch double-mode interactive design based on the microcontroller supports the intelligent control functions such as brightness gradual change and scene mode and solves the problem that the interactive mode in the prior art is single, thereby providing a user with more convenient operating experience and meeting requirements on different sleep aid scenarios.

5. Through the type-selecting solution of the red light LEDs or warm yellow light LEDs with specific wavelengths, in combination with the grounded drive circuits, the light color output matching the sleep aid requirements is achieved, the problem that the phototherapy effect is not desirable in the prior art is addressed specifically, and the functional innovation of the sleep aid device is intensified.

DESCRIPTION OF EMBODIMENTS

Specific implementations of the present disclosure will be further described in detail below in conjunction with the drawings.

I. Implementation of an Overall Architecture of a System

Figure 1:
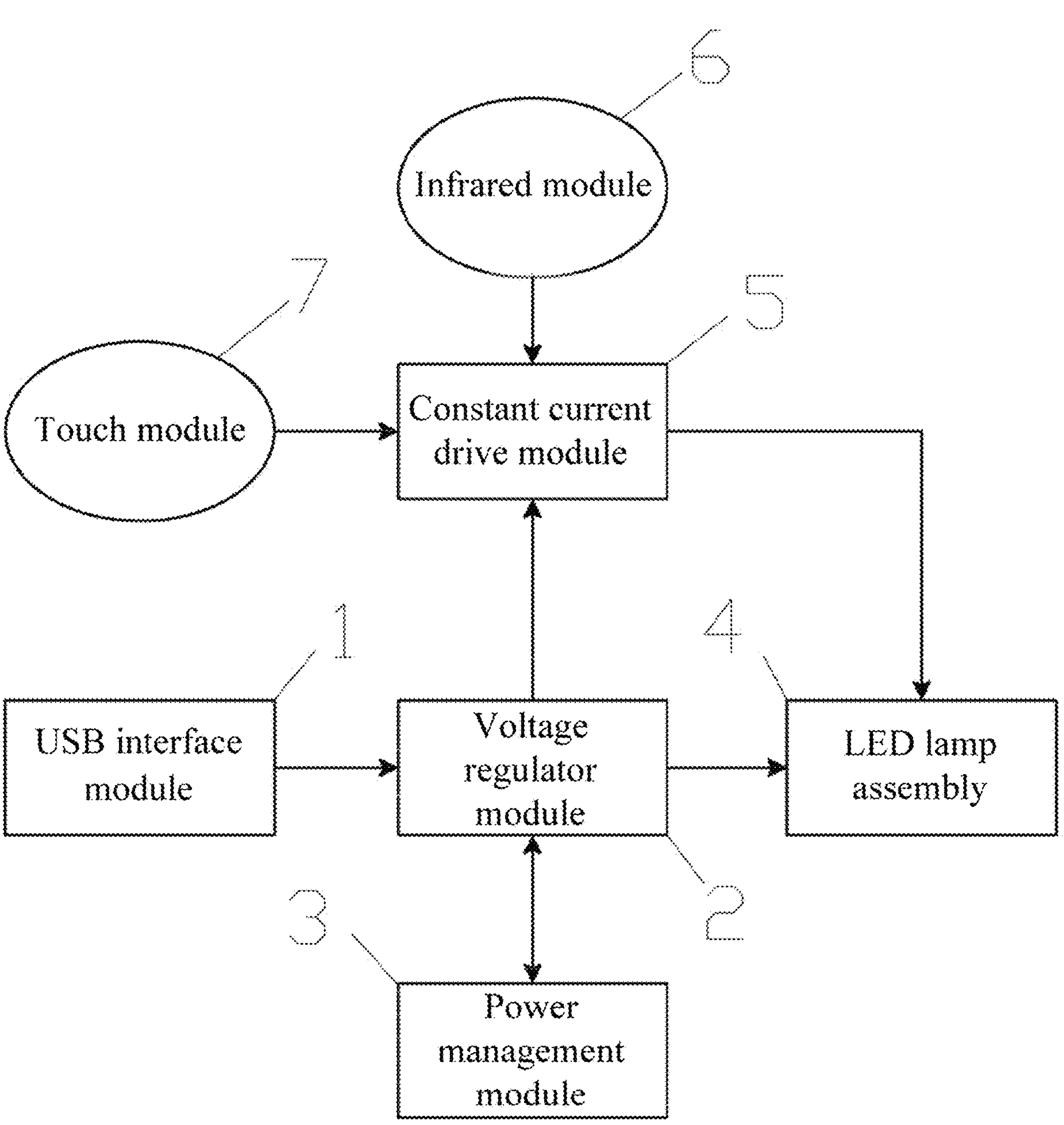
FIG. 1 is a block diagram of a system of the present disclosure.

As shown in FIG. 1, the LED control drive system achieves cooperative work in terms of functions through a modular design:

The USB interface module 1 is a TYPE-C interface, a VBUS terminal thereof is connected to an external 5V power supply, and a GND terminal thereof is grounded to provide an input voltage for the system.

A voltage regulator module 2 is directly electrically connected to the USB interface module, and an output terminal B+ of the regulator module supplies power to subsequent circuits (including a power management module 3, an LED lamp assembly 4, a constant current drive module 5, an infrared module 6, and a touch module 7) and charges a storage battery 23 as well.

A power control chip U1 (model ZW46103) of the power management module 3 is connected to a conversion circuit and a voltage feedback circuit of the voltage regulator module to monitor in real time the charge of state.

A microcontroller U2 (model ZW8P98001) of the constant current drive module 5 respectively communicates with the infrared module 6, the touch module 7, and a dimming circuit 8, and receive the user command and control the brightness of the LED lamp assembly 4.

II. Specific Implementation of the Voltage Regulator Module 2

1. Circuit Connection and Parameters of the Conversion Circuit 21

Figure 2:
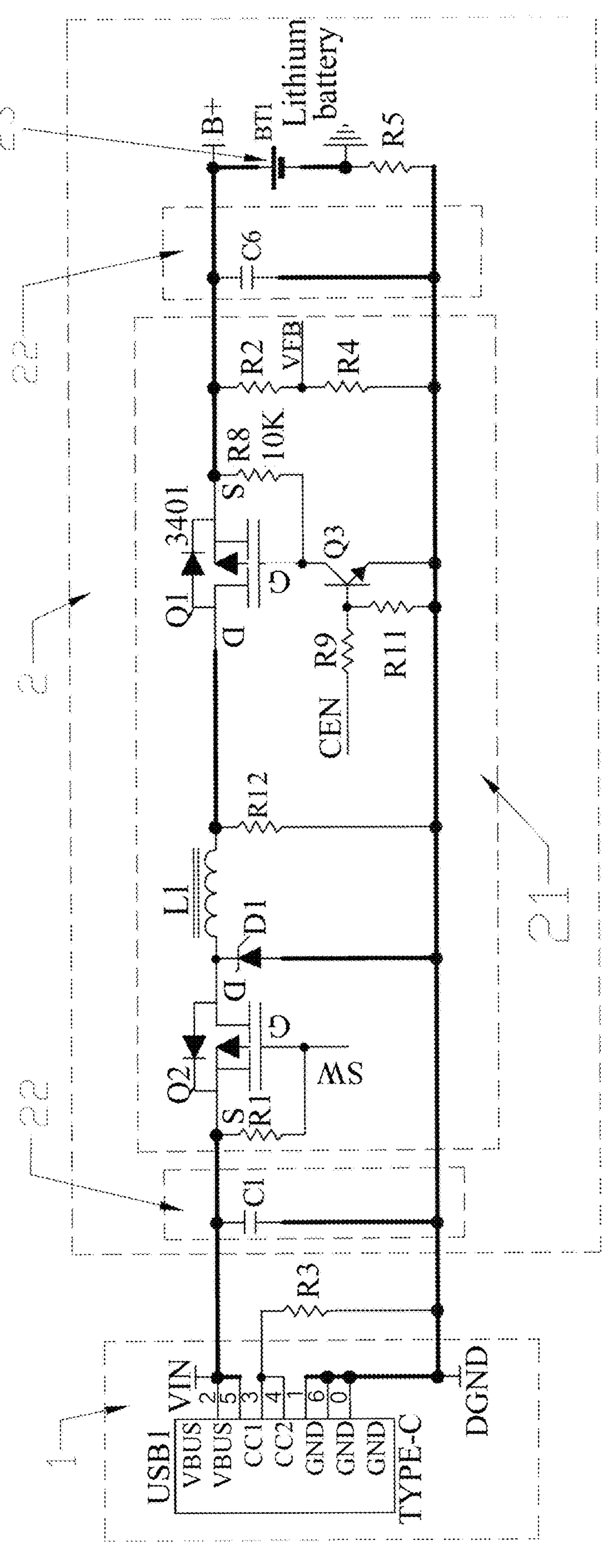
FIG. 2 is a schematic circuit diagram of a USB interface module and a voltage regulator module of the present disclosure.

As shown in FIG. 2, the conversion circuit 21 is of a buck topological structure:

A source of an N-channel MOS transistor Q2 is connected to the VBUS terminal of the USB interface module, a drain is connected to one terminal of an inductor L1 (4.7 uH/3A) and an anode of a Schottky diode D1, a gate receives a PWM signal outputted by a SW pin of the power control chip U1 through a first resistor R1 (10 kΩ, and a 5V input voltage is reduced to a 4.2V stable voltage by adjusting a duty cycle.

A drain of a P-channel MOS transistor Q1 is connected to the other terminal of the inductor L1, a source outputs the B+ voltage, and a gate controlled by the eighth resistor R8 (10 kΩ and a collector of a NPN triode Q3 (model S8050) to achieve synchronous rectification, so as to improve the conversion efficiency.

A base of the NPN triode Q3 is connected to the CEN pin of the U1 through a ninth resistor R9 (1 kΩ, an emitter is grounded, and an eleventh resistor R11 (10 kΩ is connected in series between the base and the emitter, to suppress the switching noise.

2. Implementation of the Filter Circuit 22

A first capacitor C1 (10 μF/10 V) is connected in parallel between the VBUS and the GND of the USB interface and configured to filter high frequency ripple waves.

A sixth capacitor C6 (22 μF/25 V) is connected in parallel between the B+ output terminal and the ground and configured to smooth the direct current voltage and supply power to the storage battery.

3. The Voltage Feedback Circuit 24 and the Current Sampling Circuit 25

The voltage feedback circuit is connected in series by a second resistor R2 (2 MΩ, 1%) and a fourth resistor R4 (270 KΩ, 1%) to divide the voltage to feed the B+ voltage to the VFB pin of the U1 to dynamically adjust the PWM duty cycle, so as to maintain the constant voltage.

A current sampling circuit is connected in series between a negative terminal of the storage battery and the ground through the fifth resistor R5 (50 mR, 1206, 1%) and configured to monitor in real time the discharge current.

When the USB is connected to the power supply, the CEN pin of the power control chip U1 outputs a high level, so that the NPN triode Q3 is in conduction, the P-channel MOS transistor Q1 is turned on, and the conversion circuit reduces 5 V to 4.2 V to charge the storage battery; and when the USB is disconnected, the system automatically switches to supply power to the storage battery, and the voltage feedback circuit maintains the stable voltage at the B+ terminal.

III. Specific Implementation of the Power Management Module 3

Figure 3:
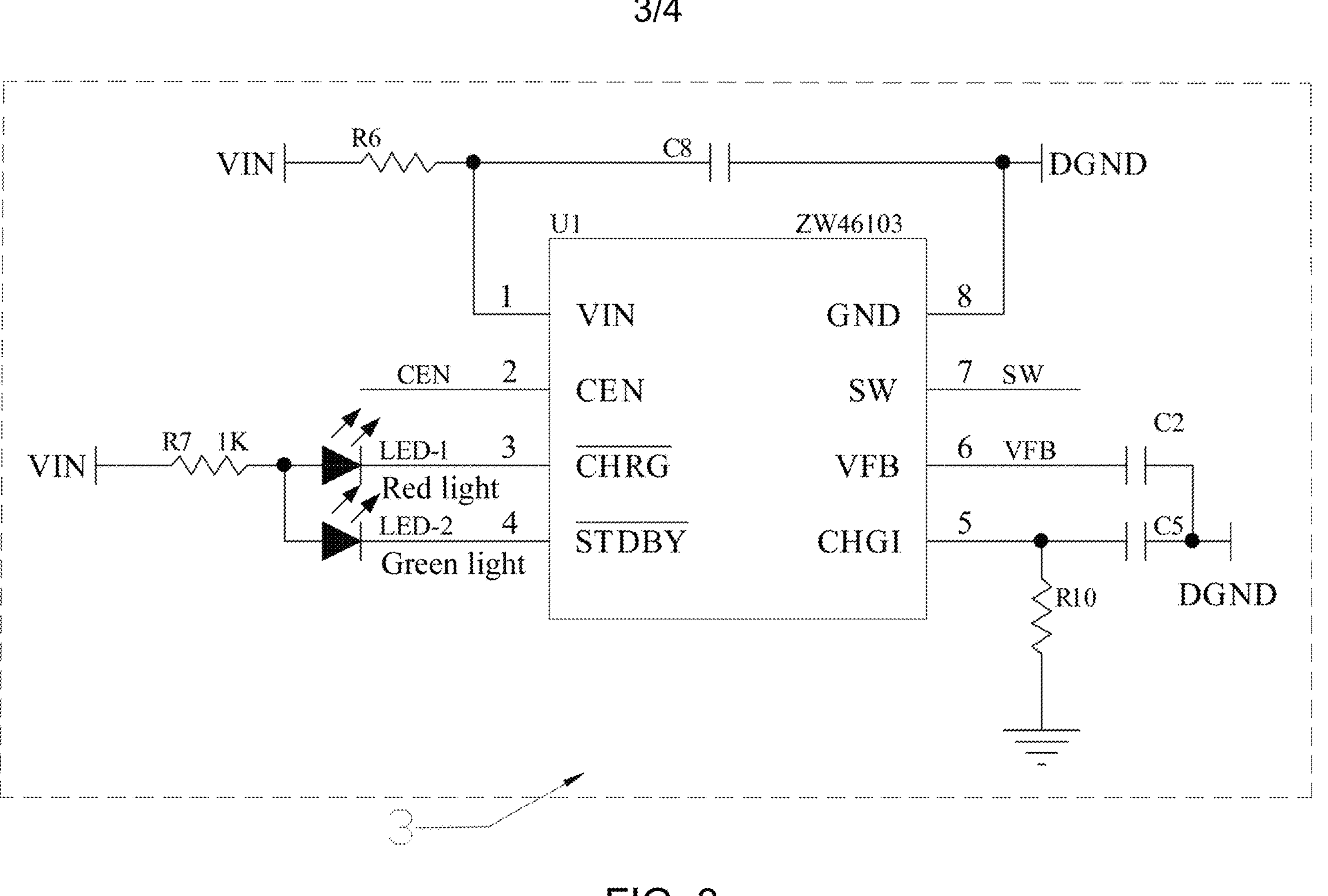
FIG. 3 is a schematic circuit diagram of a power management module of the present disclosure.
Figure 4:
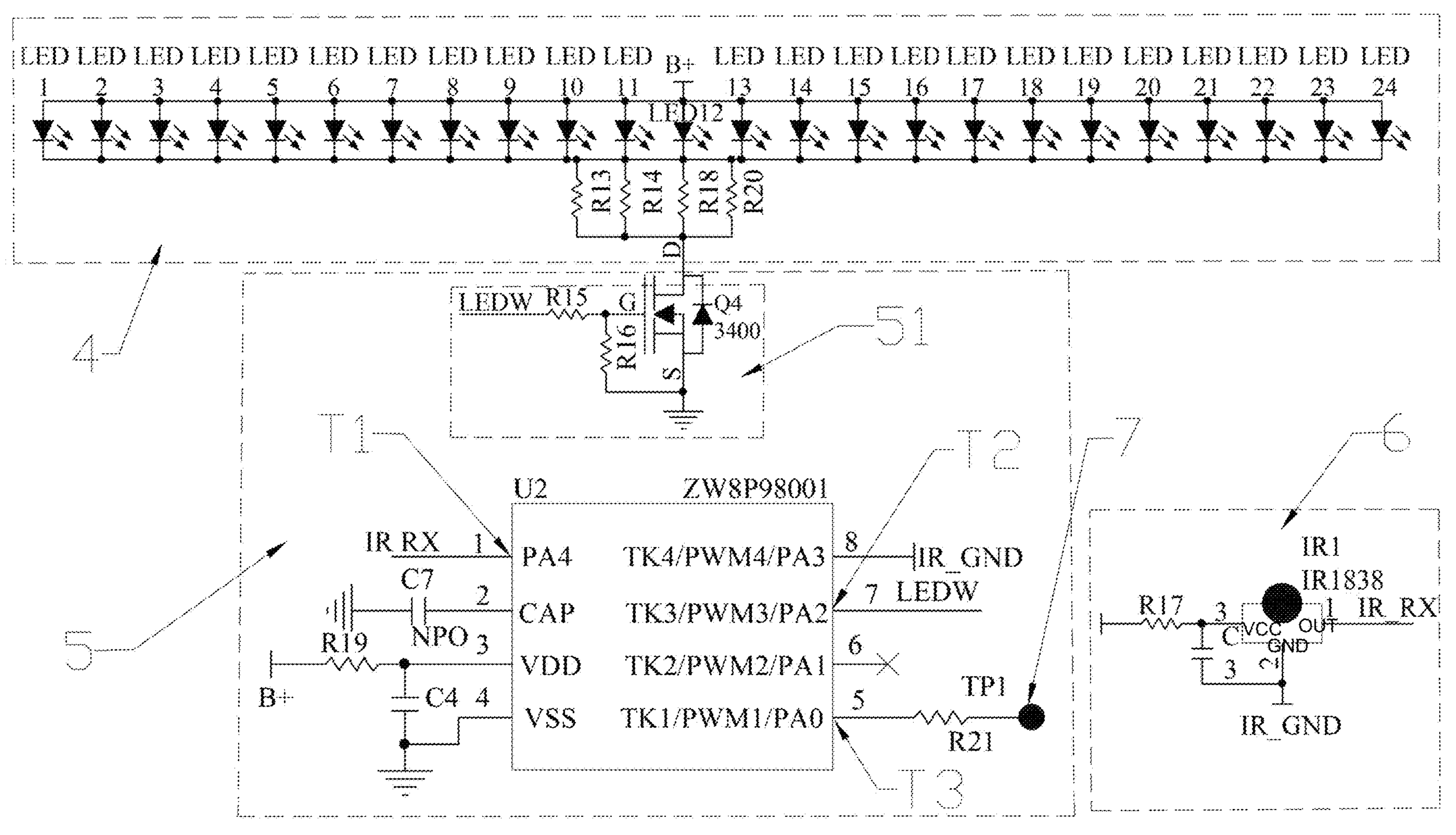
FIG. 4 is a schematic circuit diagram of an LED lamp assembly, a constant current drive module, and an infrared module of the present disclosure.

As shown in FIG. 2 and FIG. 3, a pin of the power management chip U1 is connected as follows:

the switch driver output pin SW is electrically connected to the gate of the Q2 and configured to output a 500 kHz PWM signal to control on-off of the Q2.

The enable control pin CEN is connected to the base of the Q3 through the ninth resistor R9 (1 kΩ. When the CEN is at a high level, the Q3 is in conduction, the Q1 is in conduction due to reduction of the level of the gate, and the conversion circuit is activated.

The voltage feedback regulation pin VFB is connected to a voltage division node of the R2 and R4 through a second capacitor C2 (10 nF), and compares the feedback voltage with an internal reference voltage 1.25V of the chip U1 to adjust an output voltage to 4.2 V±0.1 V.

The power input terminal VIN is connected to the VBUS terminal of the USB after being filtered by the sixth resistor R6 (10Ω) and the eighth capacitor C8 (10 μF/10 V) to ensure that the chip supplies power stably.

IV. Implementation of the LED Lamp Assembly 4 and the Constant Current Drive Module 5

1. Selection and Circuit Implementation of the LED Type

Embodiment 1: A Solution Using Red Light LEDs

LED parameters: red light LEDs with wavelengths of 625 nm+5 nm are selected, where a forward voltage typical value is 2.0 V and a rated current is 200 mA.

Grouping and Current Limiting Design:

As shown in FIG. 3, 4 groups of red light LEDs (LED-1 to LED-4) are connected in parallel, anodes of each group are connected in series to 1052 current limiting resistors (R13, R14, R18, R20), and a cathode common terminal is connected to the drain of the N-channel MOS transistor Q4 of the dimming circuit 51.

Current calculation: the voltage at the output terminal B+ of the conversion circuit is 4.2V, and the current in a single group is as follows:

I=(4.2 V-2.0 V)/10Ω=220 mA

By controlling the current within a current safe operating area of 200-250 mA through the 1002 limiting resistors, matched with PWM dimming, +3% constant current precision is achieved.

Embodiment 2: A Solution Using Yellow Light LEDs

LED parameters: yellow light LEDs with color temperatures of 1,800 K=100 K are selected, where a forward voltage typical value is 3.0V and a rated current is 150 mA.

Grouping and Current Limiting Design:

The grouping mode of the four groups of yellow light LEDs is consistent with that of the red light LEDs, and each group is connected to the 10Ω current limiting resistors, but the voltage at the B+ terminal is maintained 4.2 V: I=(4.2 V-3.0 V)/10Ω=120 mA;

The conduction time of the Q4 is adjusted based on the PWM signal outputted by the microcontroller U2, and 0-100% brightness adjustment and +3% constant current precision are achieved based on 120 mA.

Regardless of the red light LEDs or yellow light LEDs, 4 groups of parallel interfaces are reserved uniformly in a PCB welding pad, the current limiting resistors all are 1206-encapsulated 1002 resistors, and type selection (for example, medical red light LEDs and household yellow light LEDs) is achieved by welding single type LEDs during production.

2. Interface Connection and Function Implementation of the Microcontroller U2

The infrared signal receiving pin T1 is connected to the signal output terminal of the infrared module 6, a remote control command modulated by 38 kHz is identified through an internal decoding circuit, and the following functions are supported:

A, brightness adjustment: receive "+" and "−" push button signals and control the PWM duty cycle to increase and decrease with a step length of 10%;

B, mode switching: identify commands such as "deep sleep" and "relax mode", and call a corresponding light color gradient algorithm (for example, a 30 min brightness decreasing program) of the red light LEDs); and C, the PWM dimming output pin T2 is connected to the gate of the Q4 through the fifteenth resistor R15 (1 kΩ to output a 200 Hz PWM signal, where the duty cycle is adjustable from 0% to 100%, and a specific control logic is as follows:

When the duty cycle is 100%, the Q4 is in conduction continuously, and the LEDs work at the rated current; and when the duty cycle is dynamically adjusted, the average current is controlled through the pulse width to maintain the constant current characteristic (for example, the average current of the yellow light LEDs is 60 mA when the duty cycle is 50%).

The touch input pin 3 is electrically connected to the input terminal of the touch module through the twenty-first resistor R21 (1 kΩ and is internally integrated with a RC filter circuit to identify the following operations:

click operation: short press to trigger "ON/OFF" or "Mode Switch"; and long press operation: long press for 3 seconds to enter a "brightness customization" mode, and long press the touch control button to adjust the PWM duty cycle, so as to feed in real time to the LED brightness.

V. Specific Implementation of the Dimming Circuit

As shown in FIG. 3, the dimming circuit 51 uses the N-channel MOS transistor Q4 as a switching device:

The gate of the Q4 receives the PWM signal of the microcontroller through the R15 (1 kΩ, and the sixteenth resistor R16 (10 kΩ is a gate pull-down resistor to ensure reliable cut-off of the Q4.

The drain of the Q4 is connected to the cathode common terminal of the LED lamp assembly, and the source is grounded. When the PWM signal is at a high level, the Q4 is in conduction, and the LEDs emit light; and the Q4 is cut off at a low level, and 0-100% brightness adjustment is achieved by adjusting the duty cycle.

VI. Implementation of a Workflow of the System

1. Power Supply Connection and Charge

When the USB power supply is connected, the CEN pin of the U1 outputs a high level, the conversion circuit is activated to reduce 5 V to 4.2 V to charge the BT1, and the B+ terminal supplies power to the LED lamp assembly. The voltage feedback circuit samples in real time the B+ voltage to ensure a stable charging voltage.

2. User Interaction and Dimming Control

The user sends a command through an infrared remote controller or a touch panel, the infrared module 6 or the touch module 7 transmits the signal to the microcontroller U2, and the microcontroller U2 parses the command and outputs a corresponding PWM signal to the dimming circuit 51 through the PWM dimming output pin T2 to control the conduction time of the N-channel MOS transistor Q4, so as to adjust the brightness of the LED module 4.

3. Energy Management and Protection:

The current sampling circuit monitors the discharge current of the storage battery through the R5, and when the USB is disconnected, the system automatically switches to supply power by the storage battery; and when the voltage of the battery is lower than 3.5 V, the power control chip U1 controls the PWM duty cycle to decrease, and the brightness of the LEDs is reduced, and the system is turned off automatically when the voltage is lower than 3 V to prevent over discharge.

Through the above specific implementations, the system achieves highly stable power management, precise constant current drive, and intelligent interactive control, thereby effectively improving the practicality and user experience of the sleep aid device.

What is claimed is:

1. A light emitting diode (LED) control drive system for a sleep aid device, comprising:

a universal series bus (USB) interface module, being configured to receive an external input voltage, a voltage regulator module, being connected to the USB interface module, comprising a conversion circuit, a filter circuit, and a storage battery, and configured to convert the external input voltage into a stable direct current voltage and charge the storage battery, so as to provide a stable power supply basis, a power management module, comprising a power control chip, wherein the power control chip is connected to the voltage regulator module and configured to control a working state of the conversion circuit and detect in real time a charging state of the storage battery, so as to guarantee the power supply stability by dynamic regulation, an LED lamp assembly, being provided with a plurality of sleep aid LEDs, and a constant current drive module, comprising a microcontroller and a dimming circuit, the microcontroller being connected to an infrared module and a touch module and configured to receive a user input command, wherein a control terminal of the dimming circuit is connected to the microcontroller and an output terminal of the dimming circuit is connected to the LED lamp assembly, and the dimming circuit is configured to control a brightness of the LED lamp assembly according to a command of the microcontroller based on the stable power supply basis, so as to avoid a voltage fluctuation impact, wherein the conversion circuit comprises an inductor, a first N-channel metal oxide semiconductor (MOS) transistor, a Schottky diode, a second P-channel MOS transistor, an NPN triode, a first resistor, an eighth resistor, a ninth resistor, an eleventh resistor, and a twelfth resistor, a source of the first N-channel MOS transistor is electrically connected to a VIN output terminal of the USB interface module, a drain of the first N-channel MOS transistor is electrically connected to a first terminal of the inductor and a cathode of the Schottky diode, respectively, and an anode of the Schottky diode is grounded; a gate of the first N-channel MOS transistor is electrically connected to a first terminal of the first resistor, a second terminal of the first resistor is electrically connected to the source of the first N-channel MOS transistor and configured to convert a high voltage outputted by the USB interface module into a low regulated voltage by regulating a duty cycle of a pulse width modulation (PWM) signal to supply power to a subsequent circuit, a second terminal of the inductor is electrically connected to a drain of the second P-channel MOS transistor and a first terminal of the twelfth resistor, and a second terminal of the twelfth resistor is grounded; a source of the second P-channel MOS transistor is electrically connected to an output terminal of the conversion circuit and a first terminal of the eighth resistor, a gate of the second P-channel MOS transistor is connected to a second terminal of the eighth resistor and a collector of the NPN triode, and a base of the NPN triode is electrically connected to a control terminal of the power management module through the ninth resistor; an emitter of the NPN triode is electrically connected to ground and the eleventh resistor is connected in series between the base and the emitter of the NPN triode and configured to eliminate a residual charge in a base region and suppress noise interference, so as to stabilize an on-off state of the NPN triode.

2. The LED control drive system for a sleep aid device according to claim 1, wherein the LEDs are red light LEDs with wavelengths of 625 nm±5 nm or yellow light LEDs with color temperatures of 1,800 K±100 K.

3. The LED control drive system for a sleep aid device according to claim 1, wherein the filter circuit comprises a first capacitor and a sixth capacitor, a first terminal of the first capacitor is electrically connected to the VIN output terminal of the USB interface module, and a second terminal of the first capacitor is electrically connected to ground and configured to filter high frequency ripple noise in an input voltage of the USB interface module and smooth a waveform of the input voltage, so as to prevent power interference from affecting system stability, and a first terminal of the sixth capacitor is electrically connected to an output terminal of the conversion circuit and a second terminal is electrically connected to ground and configured to store electric energy outputted by the conversion circuit, supply power to the storage battery continuously during discharge of the inductor, and smooth an output voltage, so as to reduce a ripple factor of the output voltage.

4. The LED control drive system for a sleep aid device according to claim 1, wherein the voltage regulator module further comprises a voltage feedback circuit and a current sampling circuit, the voltage feedback circuit comprises a second resistor and a fourth resistor, a first terminal of the second resistor is electrically connected to an output terminal of the conversion circuit, and a second terminal of the second resistor is electrically connected to a first terminal of the fourth resistor and a voltage feedback terminal of the power control chip of the power management module; a second terminal of the fourth resistor is electrically connected to ground and configured to divide an output voltage and feed the output voltage back to the power control chip (U1), and the current sampling circuit comprises a fifth resistor, wherein the fifth resistor is connected in series between a negative terminal of the storage battery and the ground and configured to monitor in real time a discharge current of the storage battery and trigger a protection mechanism when a current exceeds a threshold.

5. The LED control drive system for a sleep aid device according to claim 4, wherein the power control chip comprises:

a switch driver output pin, being electrically connected to the gate of the first N-channel MOS transistor to output a high frequency PWM pulse signal to control the first N-channel MOS transistor;

an enable control pin, being electrically connected to a first terminal of the ninth resistor, wherein a second terminal of the ninth resistor is electrically connected to the base of the NPN triode in the conversion circuit and configured to send an enable signal and control conduction of the NPN triode, so as to achieve start-stop control of the conversion circuit; and a voltage feedback regulation pin, being electrically connected to a common node of the second resistor and the fourth resistor through a second capacitor, and configured to collect a voltage division signal of the output voltage of the conversion circuit and dynamically adjust the duty cycle of the PWM signal according to a comparison result to achieve constant voltage control.

6. The LED control drive system for a sleep aid device according to claim 1, wherein the LEDs are divided into a plurality of groups in parallel, each group of the LEDs is connected in series to current limiting resistors, and the current limiting resistors comprise a thirteenth resistor, a fourteenth resistor, an eighteenth resistor, and a twentieth resistor;

first terminals of the thirteenth resistor, the fourteenth resistor, the eighteenth resistor, and the twentieth resistor are electrically connected to cathodes of the LEDs in different groups, and second terminals thereof are commonly electrically connected to the output terminal of the conversion circuit to achieve independent constant current control of each group of the LEDs.

7. The LED control drive system for a sleep aid device according to claim 1, wherein the dimming circuit comprises a third N-channel MOS transistor, a fifteenth resistor, and a sixteenth resistor;

a first terminal of the fifteenth resistor is electrically connected to a PWM dimming output terminal of the microcontroller of the constant current drive module, and a second terminal of the fifteenth resistor is electrically connected to a gate of the third N-channel MOS transistor; a first terminal of the sixteenth resistor is electrically connected to the gate of the third N-channel MOS transistor, and a second terminal of the sixteenth resistor is electrically connected to ground; and a drain of the third N-channel MOS transistor is electrically connected to a cathode common terminal of the LED lamp assembly, and a source of the third N-channel MOS transistor is grounded.

8. The LED control drive system for a sleep aid device according to claim 7, wherein the microcontroller comprises:

an infrared signal receiving pin, being electrically connected to a signal output terminal of the infrared module and configured to receive a demodulated infrared remote control command;

a PWM dimming output pin, being electrically connected to a control terminal of the dimming circuit and configured to output a variable duty cycle of the PWM signal to adjust an overall brightness of the LED lamp assembly; and a touch input pin, being electrically connected to an input terminal of the touch module through a twenty-first resistor with 1 KΩ and configured to receive a touch operation signal.

9. The LED control drive system for a sleep aid device according to claim 1, wherein the power management module further comprises a sixth resistor and an eighth capacitor;

a first terminal of the sixth resistor is electrically connected to the VIN output terminal of the USB interface module, and a second terminal of the sixth resistor is electrically connected to a first terminal of the eighth capacitor; a second terminal of the eighth capacitor is grounded; a common node of the sixth resistor and the eighth capacitor is electrically connected to a power input terminal of the power control chip; and a ground terminal of the power control chip is directly electrically connected to ground.

* * * * *